United States Patent [19]

Cise et al.

[11] 4,104,470

[45] Aug. 1, 1978

[54] CRYSTALLIZATION PROCESS FOR CEFAZOLIN SODIUM

[75] Inventors: Michael D. Cise, Indianapolis; Harold E. Osborne, Greenwood, both of Ind.

[73] Assignee: Eli Lilly and Company, Indianapolis, Ind.

[21] Appl. No.: 803,018

[22] Filed: Jun. 3, 1977

[51] Int. Cl.² .......................................... C07D 501/36
[52] U.S. Cl. ....................................... 544/27; 424/246
[58] Field of Search ........................................... 544/27

[56] References Cited

U.S. PATENT DOCUMENTS 3,516,997  6/1970  Takano et al. ................... 260/243 C

OTHER PUBLICATIONS

Kariyone et al., The Jour. of Antibiotics, vol. XXIII [3], pp. 131–135, (Mar. 1970).

Primary Examiner—Nicholas S. Rizzo
Attorney, Agent, or Firm—William B. Scanlon; Arthur R. Whale

[57] ABSTRACT

The cephalosporin antibiotic, cefazolin sodium, is provided in the monohydrate crystalline form substantially free of other crystalline forms via addition of a concentrated solution of cefazolin acid in a water-miscible organic solvent such as DMAC to a sodium cation donor solution, e.g., sodium acetate in ethanol, wherein said sodium cation donor solution contains water in an amount sufficient to constitute 3–7 percent by volume of the mixed solutions.

7 Claims, No Drawings

CRYSTALLIZATION PROCESS FOR CEFAZOLIN SODIUM

BACKGROUND OF THE INVENTION

The cephalosporin antibiotic known as cefazolin is represented by the following structural formula.

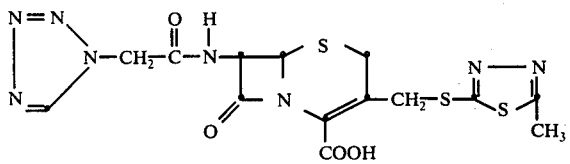

Cefazolin, U.S. Pat. No. 3,516,997 has achieved clinical importance and is widely used in the treatment and control of infectious diseases. Cefazolin sodium, cefazolin of the above formula in the sodium salt form, is administered parenterally.

This invention relates to a process for preparing cefazolin sodium as the crystalline monohydrate. In particular, this invention provides a process for preparing the crystalline monohydrate of cefazolin sodium substantially free of other crystalline forms. Various crystalline forms of cefazolin sodium have been described. For example, K. Kariyone, et. al., *The Journal of Antibiotics*, Vol. XXIII [3], 131-135, March, 1970, describes a pentahydrate designated as an α-form, and a β-form containing 1.5 mole of water of crystallization. Cefazolin sodium can also be used as a lyophilized powder or in an amorphous form.

In the manufacture of cephalosporin antibiotics it is highly desirable to produce consistently the same crystalline form of the antibiotic from batch to batch. Such consistency is difficult to achieve with some cephalosporin antibiotics, particularly when a certain crystalline form is desired and other crystalline forms of the same antibiotic are capable of formation in the process.

Among the crystalline forms of cefazolin sodium the monohydrate is highly desirable as the pharmaceutical form. The crystalline monohydrate has also been designated as the β-form, however, it is distinct from the β-form described by K. Kariyone et. al., supra. As noted above, the β-form described by Kariyone et al. is a 1.5 hydrate while the crystalline form provided by the process of this invention is a monohydrate.

Prior to this invention the preparation of the monohydrate crystalline form of cefazolin sodium has been difficult to achieve with any consistency. Commonly, the preparation of cefazolin sodium in mixtures of the various hydrated forms occurs. Such preparations containing mixtures of crystalline forms are generally unsuitable for pharmaceutical use because of instability on storage and during handling in the manufacturing process. For example, the higher hydrates tend to lose water of crystallization and thus crystallinity. Also, the water lost from the higher hydrates tends to cause instability of the product on storage. Accordingly, there is a need for a method for preparing cefazolin sodium in a single pharmaceutically acceptable crystalline form.

SUMMARY OF THE INVENTION

According to the process of this invention, substantially pure cefazolin is converted to the monohydrate crystalline sodium salt in a one-step salt-forming crystallization process. The process comprises the addition of a solution of cefazolin free acid in a water-miscible organic solvent such as dimethylacetamide at a concentration of between about 250 and about 500 mg./ml. to a solution of a sodium cation donor in a water-miscible organic solvent containing water and containing between about 10 and 20 percent excess of the molar equivalent of the sodium cation donor. Sodium cation donors are illustratively sodium salts of carboxylic acids, for example, sodium acetate, sodium 2-ethylhexanoate, or inorganic sodium ion donors such as sodium hydroxide and sodium carbonate. The sodium cation donor solution contains sufficient water to achieve a concentration of water in the combined solutions following addition of between about 3 percent and about 7 percent by volume. The cefazolin free acid solution is preferably substantially anhydrous.

The rate of addition of the cefazolin free acid solution to the sodium ion donor solution controls the concentration of water in the mixed solutions at a level sufficient to form the monohydrate. The addition of the cefazolin free acid solution to the sodium donor solution is carried out at a temperature between about 20° and about 25° C.

DETAILED DESCRIPTION

This invention provides a process for preparing cefazolin sodium as the monohydrate crystalline form substantially free of other hydrated crystalline forms and the anhydrous form. The monohydrate crystalline form obtained in the process has stability and handling characteristics which render it a desirable pharmaceutical form of the antibiotic salt. For example, the monohydrate crystals are obtained in the process in high yields as granular crystalline material, the individual crystals of which are greater than 100 microns in size. The granular monohydrate crystals obtained in the process are readily filtered and, when dry, form a freely flowing crystalline powder. Further, in contrast to other crystalline hydrated forms, for example the pentahydrate, the monohydrate provided by this invention retains its water of hydration and, therefore, remains stable on storage. The pentahydrate, on the other hand, loses water of crystallization and is less stable on storage.

The monohydrate crystalline form of cefazolin sodium which is obtained in the process of this invention is characterized and is distinguished from other crystalline forms by its x-ray diffraction pattern shown below. Copper/nickel radiation of wave length λ 1.4505 was used. The column headed ($d$) is the reading in angstrom units and the column headed $I/I_1$ is the relative intensity.

| d | $I/I_1$ |
|---|---|
| 18.39 | .30 |
| 10.39 | .32 |
| 9.11 | .55 |
| 8.00 | .27 |
| 6.91 | .41 |
| 6.06 | .18 |
| 5.36 | .45 |
| 4.95 | .18 |
| 4.60 | .45 |
| 4.48 | .77 |
| 4.38 | .50 |
| 4.23 | .45 |
| 4.06 | 1.00 |
| 3.83 | .68 |
| 3.77 | .23 |
| 3.63 | .50 |
| 3.50 | .64 |
| 3.38 | .55 |
| 3.22 | .41 |

-continued

| d | I/I$_1$ |
|---|---|
| 3.13 | .32 |
| 3.02 | .41 |
| 2.93 | .36 |
| 2.86 | .14 |
| 2.78 | .27 |
| 2.71 | .09 |
| 2.53 | .36 |
| 2.47 | .36 |
| 2.39 | .23 |
| 2.34 | .14 |
| 2.30 | .23 |
| 2.12 | .18 |
| 2.04 | .27 |
| 1.99 | .05 |
| 1.95 | .09 |
| 1.82 | .09 |
| 1.76 | .09 |
| 1.70 | .14 |
| 1.66 | .05 |
| 1.61 | .05 |
| 1.59 | .05 |

The process of this invention may be characterized as a one-step salt-forming crystallization process wherein cefazolin as the free acid is converted to the sodium salt which is obtained as a granular crystalline precipitate of the monohydrate substantially free of other crystalline or amorphous forms. The process of this invention is carried out by adding a solution of substantially pure cefazolin acid in a water-miscible organic solvent at a concentration of between about 250 mg./ml. and about 500 mg./ml. to a solution of a sodium ion donor in a water-miscible organic solvent containing water and the sodium ion donor substance in an amount sufficient to provide one equivalent and preferably between about 10 and about 20 percent molar excess with respect to cefazolin free acid.

The process can be carried out at a temperature between about 10° and about 35° C. and preferably between about 20° and about 25° C.

The cefazolin free acid solution is preferably a concentrated, substantially anhydrous solution although minor amounts of water are tolerated in the process. The amount of water employed in the sodium ion donor solution is an amount sufficient to provide a concentration of water in the combined solutions following completion of the addition of between about 3 percent and about 7 percent by volume. Preferably, the final concentration of water in the total mix is between about 4 and about 6 percent by volume of the total mix. Higher concentrations of water in the combined solutions result in lower yields of the monohydrate crystalline form because of formation and co-precipitation of the pentahydrate form. Also, a concentration of water in the total mix which is below about 3 percent yields an amorphous form of the sodium salt at the expense of the monohydrate form.

The concentration of the sodium ion donor solution is not critical; however, the large volumes associated with the use of dilute solutions are to be avoided for best results. The sodium ion donor solution preferably contains between about a 10 and about a 20 percent excess of the equivalent amount of sodium ion.

Sodium ion donors which can be employed in the process of this invention include the sodium salts of carboxylic acids, which acids are weaker acids than is cefazolin and include, for example, sodium acetate, sodium propionate, sodium citrate, sodium lactate, sodium 2-ethyl hexanoate, and like sodium carboxylates; and inorganic sodium ion donors such as sodium hydroxide and sodium carbonate. Preferred sodium ion donors are sodium acetate and sodium 2-ethylhexanoate.

Water-miscible organic solvents which can be employed in preparing the concentrated solutions of cefazolin free acid are dimethylacetamide, dimethylformamide, dimethylsulfoxide, acetonitrile, and isopropanol. The preferred water-miscible solvent for preparing the cefazolin solution is dimethylacetamide. High concentrations of the acid can be achieved in this solvent. When dimethylformamide and dimethylacetamide are used as solvents, the addition of a small amount of acetic acid is benefical since any traces of basic amines in the solvents are neutralized.

Water-misible solvents which can be used to prepare the sodium ion donor solution are the lower alcohols such as methanol, ethanol, and isopropanol; and the ketones such as acetone and methylethyl ketone.

The concentrated solution of cefazolin free acid is added slowly to the water containing sodium ion donor solution with vigorous agitation in order to maintain a concentration of the acid relative to the water concentration during addition which favors monohydrate formation. The addition of the cefazolin free acid solution is carried out continuously over between about 2 and about 2.5 hours. The mix is maintained at about 20° C. to about 25° C. throughout the addition and also is vigorously agitated throughout. During addition of the acid, the monohydrate of sodium cefazolin begins to crystallize from the mix. After addition is complete the crystalline slurry is continuously agitated for between about 3 and about 5 hours to complete crystallization and crystal development.

The crystals of monohydrate are harvested from the crystalline slurry by filtration, centrifugation or other suitable separation method and are washed and dried. The crystal mass is washed with a suitable organic liquid, preferably 95 percent ethanol.

The cefazolin sodium monohydrate can be stored for later use in the preparation of pharmaceutical formulations. For example, the crystalline monohydrate can be made up into unit dosage forms for filling into ampoules.

The following examples are provided to further illustrate the process of this invention and are not intended to be limiting thereof.

EXAMPLE 1

A solution of 9.2 g. of cefazolin in 20 ml. of dimethylacetamide containing 0.5 ml. of glacial acetic acid was added continuously with stirring over a two hour period to a solution of 2.0 g. of anhydrous sodium acetate in 122.5 ml. of absolute ethyl alcohol containing 7.5 ml. of water. During the addition, a temperature of 20°–25° C. was maintained. After the addition was complete, the crystalline slurry of the monohydrate crystals was stirred for four hours and was then filtered. The cefazolin sodium monohydrate was washed on the filter with 95 percent ethyl alcohol and dried. Weight, 8.9 g.

EXAMPLE 2

A solution of 4.56 g. of cefazolin in 9 ml. of dimethylacetamide was added continuously for two hours with stirring to a solution of excess sodium 2-ethylhexanoate in 98 ml. of ethyl alcohol containing 7 ml. of water. During the addition the temperature was maintained between 20° and 25° C. After the addition was complete the crystalline slurry was stirred for three hours and was then filtered. The crystalline mass of cefazolin sodium monohydrate was washed with ethyl alcohol and dried. The weight of dried crystals was 4.7 g.

We claim:

1. A process for preparing cefazolin sodium in the monohydrate crystalline form substantially free of other crystalline forms which comprises adding at a temperature between about 10° C. and about 35° C. a solution of substantially pure cefazolin acid in a water-miscible organic solvent selected from the group consisting of dimethylacetamide, dimethylformamide, dimethylsulfoxide, acetonitrile, and isopropanol, said solution having a concentration of cefazolin acid of between about 250 mg./ml. and about 500 mg./ml.; to a solution of a sodium ion donor substance in a water-miscible organic solvent selected from the group consisting of methanol, ethanol, isopropanol, acetone, and methylethyl ketone, wherein said sodium ion donor substance is selected from the group consisting of sodium acetate, sodium propionate, sodium citrate, sodium lactate, sodium 2-ethylhexanoate, sodium hydroxide and sodium carbonate; said sodium ion donor solution containing water in an amount sufficient to constitute between about 3 and about 7 percent by volume of the mixed solutions following addition, and wherein said addition is carried out for between about 2.0 hours and about 2.5 hours.

2. The process of claim 1 wherein the water-miscible solvent of the cefazolin acid solution is dimethylformamide or dimethylacetamide.

3. The process of claim 1 wherein the sodium ion donor substance is sodium acetate or sodium 2-ethylhexanoate.

4. The process of claim 1 wherein the water-miscible solvent for the sodium ion donor is ethanol or isopropanol.

5. The process of claim 1 wherein the addition of the cefazolin acid solution is carried out at a temperature between about 20° C. and about 25° C.

6. The process of claim 1 wherein the sodium ion donor solution contains water in an amount sufficient to achieve a concentration of water in the mixed solutions following addition of between about 4 and about 6 percent by volume.

7. The process of claim 6 wherein the water-miscible solvent of the cefazolin acid solution is dimethylacetamide, the water-miscible solvent of the sodium ion donor is ethanol, the sodium ion donor is sodium acetate, and the addition of the cefazolin acid solution is carried out at a temperature between about 20° C. and about 25° C. continuously for two hours.

* * * * *